United States Patent [19]
Bresler et al.

[11] Patent Number: 6,030,417
[45] Date of Patent: Feb. 29, 2000

[54] HIP PROSTHESIS

[75] Inventors: Franck Bresler, Nancy; Philippe Catier, Pace; Philippe Caudal, La Croix-Valmer; Jean-Marie Francois, Marienthal; Jean Godefroy, Ayze, all of France; Henri Horoszowski, Ramat Chen, Israel; Daniel Mole, Nancy; Paul Rivat, Saint-Peray, both of France

[73] Assignee: Advanced Technical Fabrication, Marignier, France

[21] Appl. No.: 08/776,964

[22] PCT Filed: Aug. 10, 1995

[86] PCT No.: PCT/FR95/01072

§ 371 Date: Feb. 12, 1997

§ 102(e) Date: Feb. 12, 1997

[87] PCT Pub. No.: WO96/04868

PCT Pub. Date: Feb. 22, 1996

[30]     Foreign Application Priority Data

Aug. 12, 1994  [FR]  France ................................. 94 10125

[51] Int. Cl.[7] ........................................................ A61F 2/36
[52] U.S. Cl. ............................................................... 623/23
[58] Field of Search ..................... 623/23, 22, 19

[56]      References Cited

FOREIGN PATENT DOCUMENTS

| | | |
|---|---|---|
| 0 038 908 | 11/1981 | European Pat. Off. . |
| 0 128 036 | 12/1984 | European Pat. Off. . |
| 0 222 236 A1 | 5/1987 | European Pat. Off. ................. 623/23 |
| 0 528 284 | 2/1993 | European Pat. Off. . |
| 2 618 667 | 2/1989 | France . |
| 2 660 855 | 10/1991 | France . |
| 2 676 914 | 12/1992 | France . |
| 38 29 361 | 8/1989 | Germany . |
| WO 91/18560 | 12/1991 | WIPO . |

*Primary Examiner*—David H. Willse
*Attorney, Agent, or Firm*—Ratner & Prestia

[57]     ABSTRACT

The prosthesis of the invention comprises a shaft (1) with its upper end (3) linked to a neck (2) connecting it to a spherical joint head. The shaft (1) comprises a proximal area (H1, H2) with a reversed spiral double twist, over a length substantially equal to one third or half of the length (H) of the shaft (1). The proximal segment (H2) of the proximal area and the distal area (H3) are generally rectilinear in the antero-posterior plane, while the distal segment (H1) of the proximal area is curved with the center offset frontwards. The invention provides a prosthesis that fits more effectively in the medullary channel and does not need cement to fix it.

10 Claims, 5 Drawing Sheets

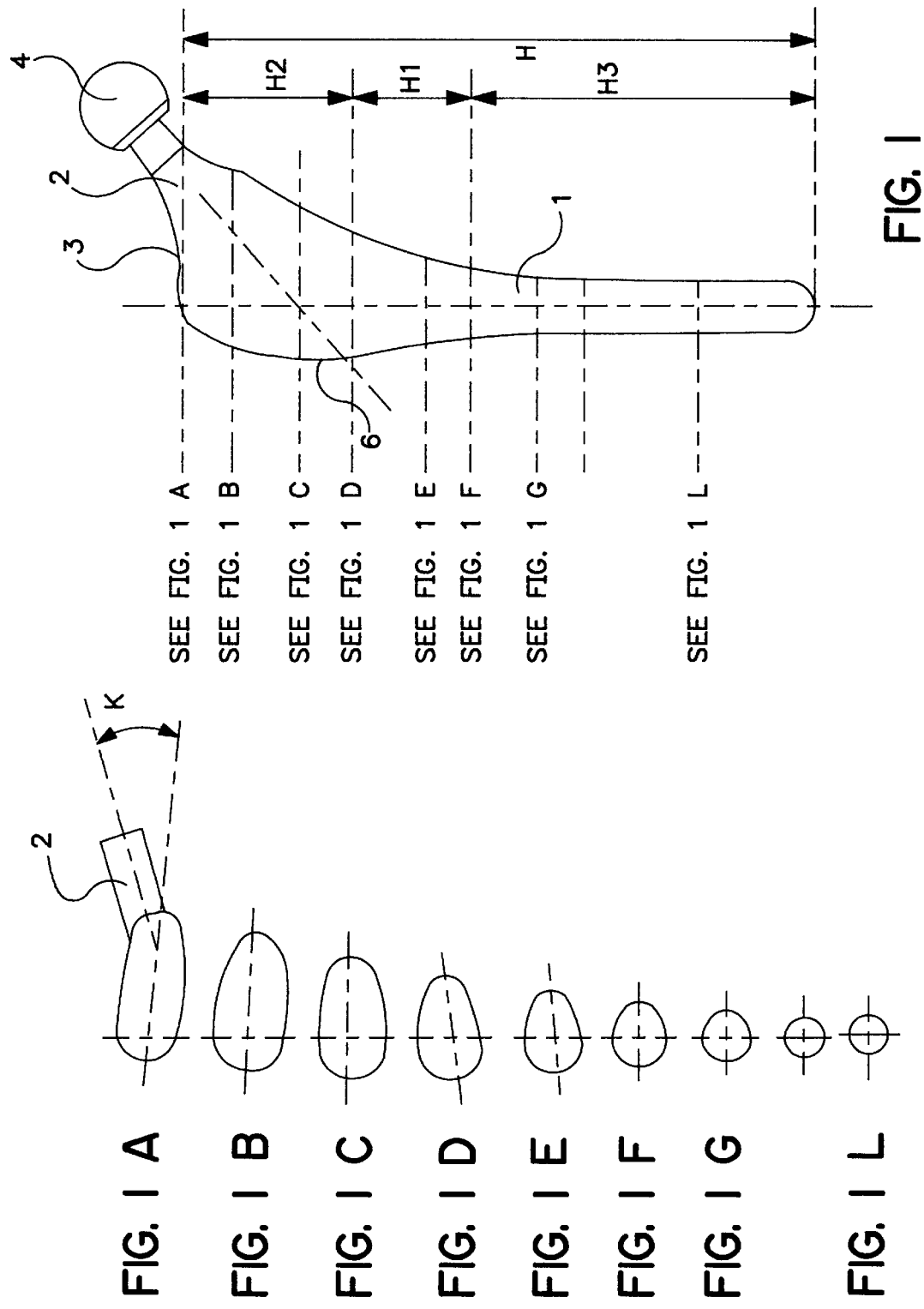

HIP PROSTHESIS

TECHNICAL FIELD OF THE INVENTION

The invention concerns hip prostheses including a rod shaped to be inserted into the medullary canal of a femur, and a neck joined to the upper end of the rod to connect it to a spherical joint head.

Various forms of hip prostheses have been proposed over the years, with rods having various curvatures.

In one prior art a hip prosthesis, for example, has a rod with a single curvature in the anterior-posterior plane with the centre offset to the posterior or anterior side. It seems that a prosthesis of this kind is incorrectly centred in the diaphysis area, which can be a cause of pain.

Prostheses, like that described in document FR-A-2 660 855, have a rod which is substantially straight in the anterior-posterior plane. These prostheses are also subject to incorrect centring which can cause pain and the transmission of mechanical loads to the femur is not well distributed.

Document EP-A-0 038 908 proposes another form of prosthesis in which the rod, in the proximal region, is curved with the centre of curvature displaced towards the anterior end, whereas the curvature of the distal region of the rod has a centre of curvature displaced towards the posterior end. This type of prosthesis is difficult to fit, because of these curvatures, and also difficult to remove. Centring is difficult and often incorrect.

Documents FR-A-2 618 667 and FR-A-2 676 914 describe left femur prostheses in which the rod, in its proximal area has a single righthanded spiral twist.

Document WO-A-91 18560 describes a right femur prosthesis the proximal area of which has a single lefthanded spiral twist.

In these documents the single spiral twist is in the direction of the anteversion of the neck.

On the other hand, documents EP-A-0 128 036 and DE-A-38 29 361 both describe a left femur prosthesis the proximal part of which has a single lefthanded spiral twist. In document EP-A-0 128 036, this single spiral twist is associated with slight posterior curvature of the distal part of the rod, whereas the proximal part of the rod is substantially straight in the anterior-posterior plane.

It appears that the prostheses described in the above documents, with a single spiral twist, are not a sufficiently effective fit in the medullary canal of the femur to achieve the necessary long-term stability and durability of the prosthesis.

SUMMARY OF THE INVENTION

The problem to which the present invention is addressed is that of defining a new prosthesis structure, which, whilst it can be cemented into the femur, can be fitted without cementing in most cases. Despite the lack of cement, the attachment of the prosthesis must be mechanically strong, and the stability of the prosthesis must be improved.

The aim is:

to distribute bending and torsion loads between the prosthesis and the bone optimally in the metaphysis part of the prosthesis, to immobilise the prosthesis in all planes of the space in the metaphysis area, to make the gap between the metaphysis part of the prosthesis and the corresponding surface of the bone of substantially constant size, to centre the rod as a whole in the cavity receiving it in the femur, both in the frontal plane and in the anterior-posterior plane, to optimise the ratio between the section of the distal part of the rod of the prosthesis and the section of the canal of the diaphysis part of the femur, to prevent points of contact with the rod causing pain, to eliminate the transmission of loads by the distal part of the rod in the diaphysis part of the femur.

To this end, the prosthesis has a rod with a different shape than prior art rods, some features of the shape of the rod going directly against received wisdom in this art. Accordingly, the invention provides a hip prosthesis including a rod adapted to be inserted and fixed into the medullary canal of a femur, a neck joined to the upper end of the rod to join it to a spherical joint head, the rod having an oblong transverse section proximal area extending from the upper end on either side of an external shoulder to a transition area below the external shoulder and followed by a distal area, the rod being curved in the lateral plane with a centre of curvature offset towards the saggital plane, the proximal area of the rod having a curved portion, in the anterior-posterior plane, with the centre of curvature offset towards the front; the oblong transverse section proximal area comprises two adjacent segments with opposite spiral twists:

a proximal segment having a righthanded spiral twist in a prosthesis for a right femur and a lefthanded spiral twist in a prosthesis for a left femur, a distal segment having a lefthanded spiral twist in a prosthesis for a right femur, and a righthanded spiral twist in a prosthesis for a left femur.

It appears that a prosthesis of this kind can be easily inserted into the medullary canal, with substantially improved immobilisation in the metaphysis area.

In an advantageous embodiment, the proximal segment and the distal segment of the oblong transverse section proximal area are joined together substantially in the area containing the external shoulder.

In a preferred embodiment, in the anterior-posterior plane, the proximal segment of the proximal area of the rod is substantially straight, whereas the distal segment of the proximal area of the rod is curved with the centre of curvature offset towards the front. The distal area of the rod is also substantially straight in the anterior-posterior plane.

The neck advantageously has an anteversion at an angle of approximately 10°.

BRIEF DESCRIPTION OF THE DRAWINGS

Further objects, features and advantages of the present invention will emerge from the following description of specific embodiments, given with reference to the appended drawings in which:

FIG. 1 shows a plan view of a left prosthesis from the rear, combined with nine transverse sections along the prosthesis rod;

DESCRIPTION OF THE PREFERRED EMBODIMENTS

As shown in the figures, the hip prosthesis of the invention includes a rod 1 adapted to be inserted and fixed into the medullary canal of a femur, and a neck 2 joined to the upper end 3 of the rod 1 in order to join it to a spherical joint head 4.

The rod 1 has a non-linear shape which varies in section and in orientation according to the position along its height H.

There is a proximal area, near the neck 2, and a distal area farther from the neck 2. The distal area has a height H3 in FIG. 1, whereas the proximal area is referenced H1 and H2.

Figure 7:
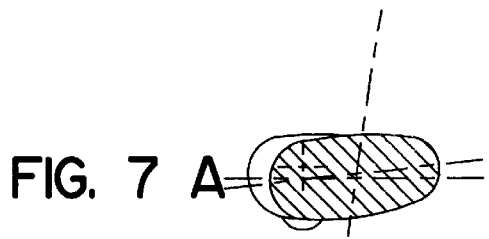
FIG. 7 is a plan view of a front view of a preferred embodiment of a right prosthesis of the invention combined with eight successive transverse sections along the prosthesis rod.
Figure 7:
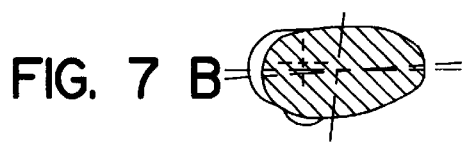
Figure 7:
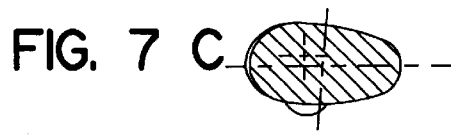
Figure 7:
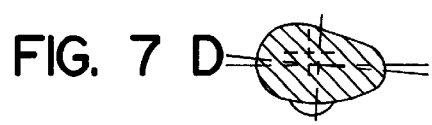
Figure 7:
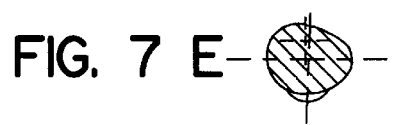
Figure 7:
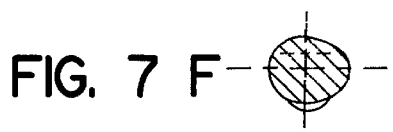
Figure 7:
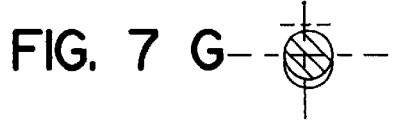
Figure 7:
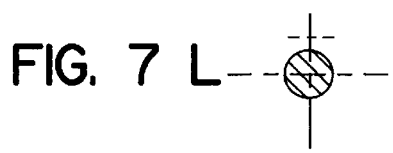
Figure 7:
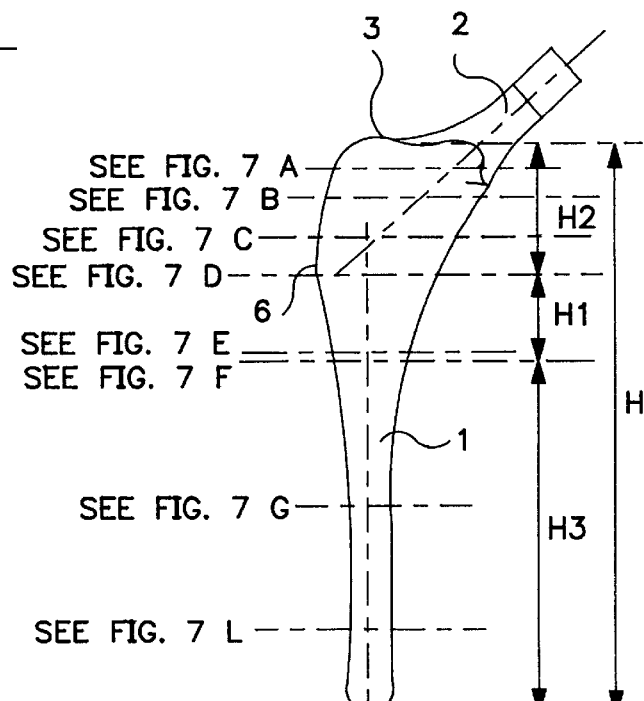
Figure 8:
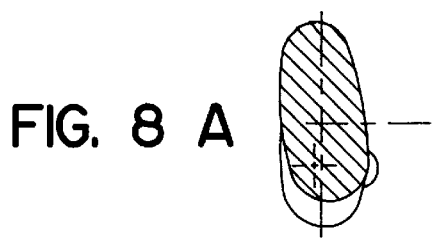
FIG. 8 is a view of the outside face of the prosthesis from FIG. 7, associated with the same successive transverse sections.
Figure 8:
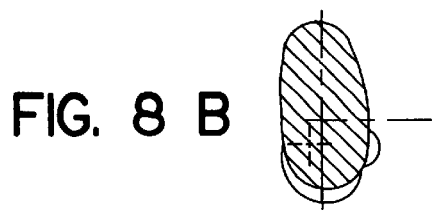
Figure 8:
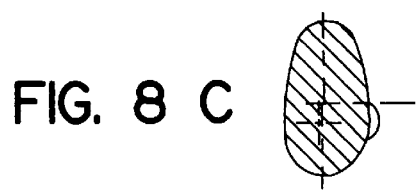
Figure 8:
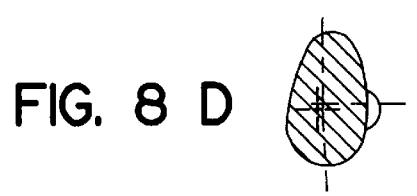
Figure 8:
Figure 8:
Figure 8:
Figure 8:
Figure 8:
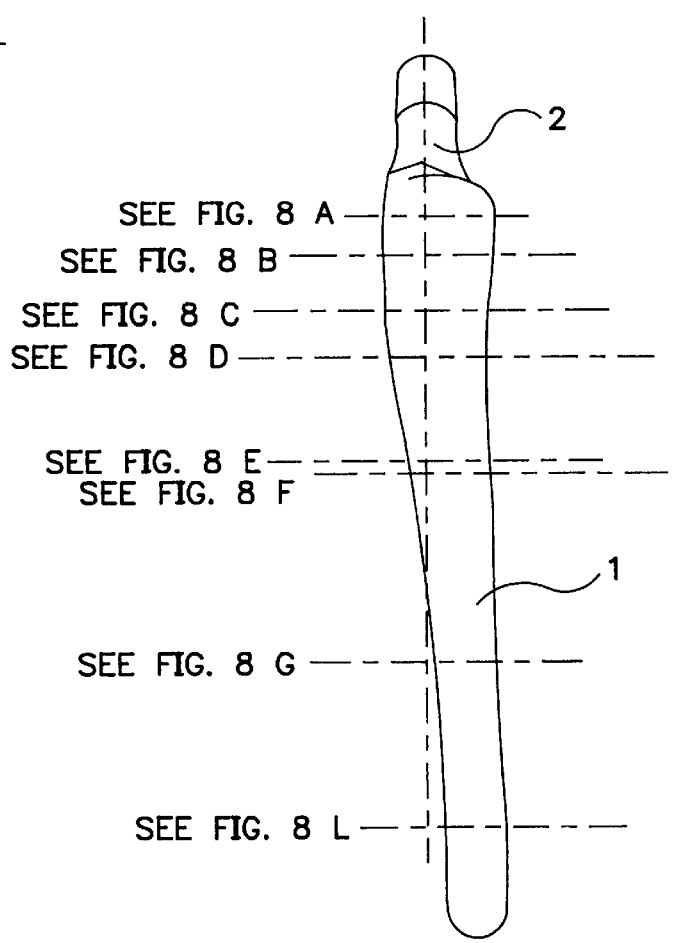

The proximal area H1+H2 of the rod 1 has a non-circular, advantageously oblong transverse section shown in the lefthand part of FIGS. 1, 7 and 8. These figures show, starting from the upper end 3, a top section A, a first intermediate section B, a second intermediate section C, a third intermediate section D, a fourth intermediate section E and a transition section F. These transverse sections A, B, C, D, E and F have an elongate, for example oblong shape, with respective major axes progressively pivoting at successive positions along the longitudinal axis of the rod 1. This pivoting defines spiral twists in the proximal area H1+H2 of the rod 1.

The proximal area H1+H2 extends, from the upper end 3, on either side of an external shoulder 6, to a transition area below the external shoulder 6 illustrated by the transition section F. The proximal area is followed by the distal area H3, the transverse sections of which, for example the sections G and L, are generally circular.

As shown in the lefthand part of FIGS. 1 and 7, the rod 1 has a curvature, in the lateral plane, with the centre of curvature offset towards the saggital plane.

The proximal area H1+H2 of the rod 1 comprises a proximal segment H2, near the neck 2, and a distal segment H1 farther from the neck 2. The proximal segment H2 has a righthanded spiral twist in a prosthesis for a right femur, and a lefthanded spiral twist in a prosthesis for a left femur. Accordingly, in FIG. 1, the successive transverse sections A, B, C and D show the lefthanded spiral twist for the left prosthesis, whereas, in FIG. 7, the same transverse sections A, B, C and D show the righthanded spiral twist for the right prosthesis.

The distal segment H1 has a lefthanded spiral twist in a prosthesis for a right femur and a righthanded spiral twist in a prosthesis for a left femur. Accordingly, in FIG. 1, the successive transverse sections D, E and F show the righthanded spiral twist for a left prosthesis in the distal segment H1, whereas, in FIG. 7, the same sections D, E and F show the lefthanded spiral twist for a right prosthesis in the distal segment H1.

In the embodiment shown in FIGS. 7 and 8, the proximal segment H2 and the distal segment H1 of the proximal area with an oblong transverse section advantageously merge substantially in the area containing the external shoulder 6.

In the embodiment shown in FIGS. 7 and 8, the proximal segment H2 has a spiral twist with an overall twist angle between about 9° and about 13°, advantageously about 11°. Likewise, the distal segment H1 has a spiral twist with an overall twist angle between 3° and 6°, advantageously about 5°.

The distal segment H1 is slightly shorter than the proximal segment H2.

The proximal or metaphysis area H1+H2, including the double spiral twist previously described, can have a length H1+H2 between one half and one third the total length H of the rod 1, in a standard prosthesis. In a prosthesis with a longer rod, for example for a replacement, this proportion varies according to the chosen length of the rod.

Figure 2:
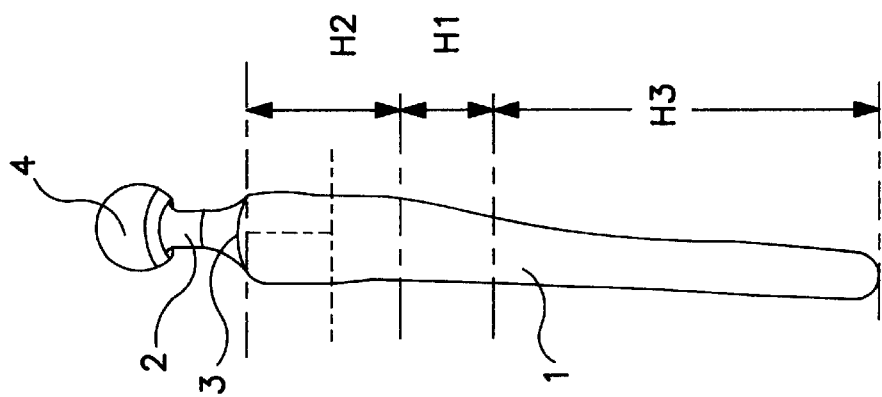
FIG. 2 shows a plan view of the outside face of the left prosthesis from FIG. 1.
Figure 5:
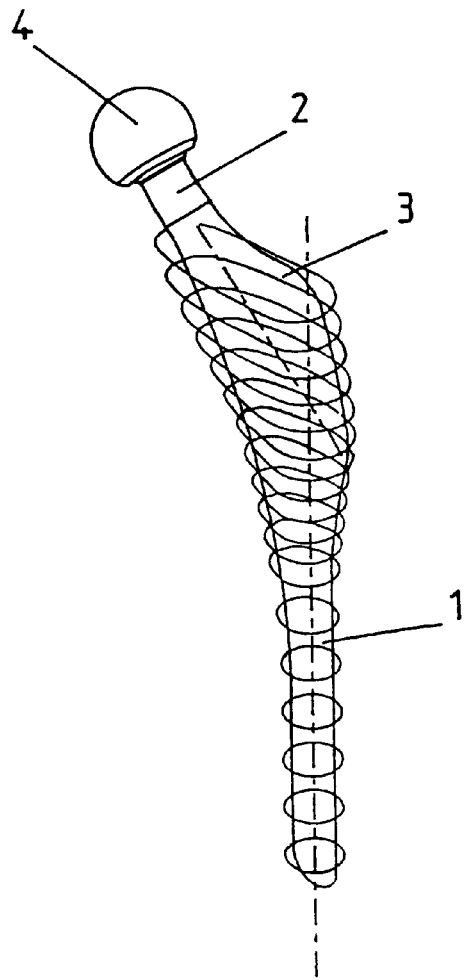
FIG. 5 is a diagrammatic perspective view of the prosthesis from FIG. 1, showing the rotation of the successive sections.
Figure 6:
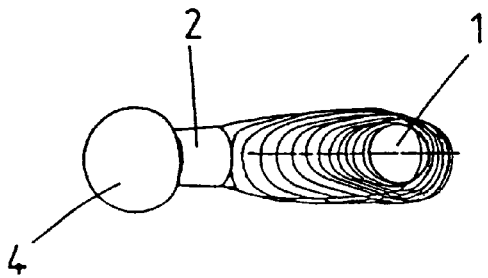
FIG. 6 is a diagrammatic top view of the prosthesis from FIG. 1.

The proximal or metaphysis area H1+H2 including the double spiral twist can be generally straight in the anterior-posterior plane, as shown in the FIG. 2 embodiment. This metaphysis area naturally has an inward curvature in the transverse plane, as shown in FIG. 1.

Figure 4:
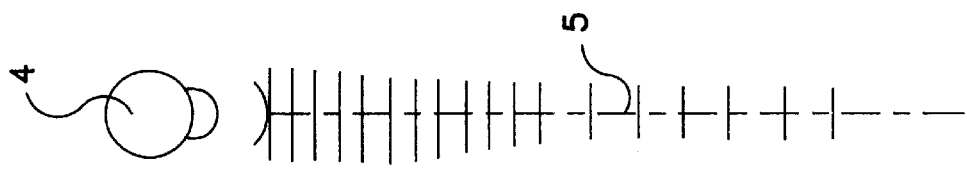
FIG. 4 is a diagrammatic representation of the inside lateral face of the prosthesis from FIG. 1.
Figure 3:
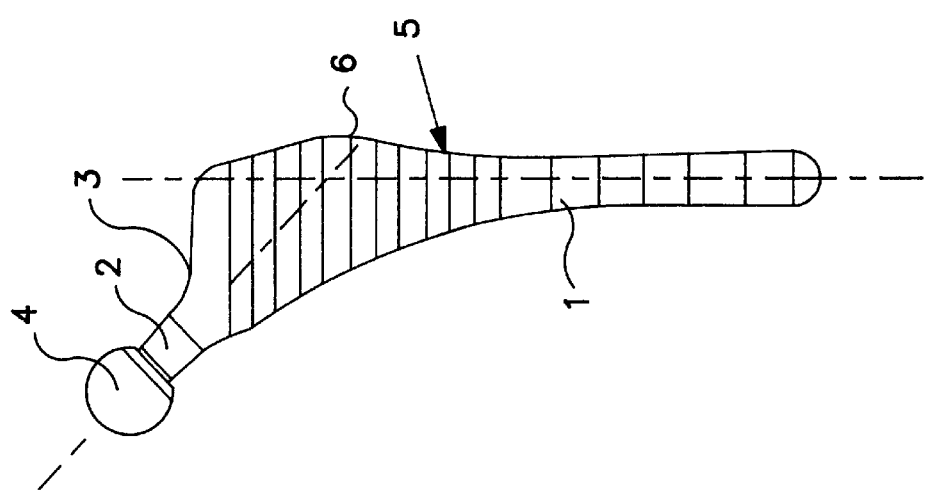
FIG. 3 is a front view of the prosthesis from FIG. 1.

In the embodiment shown in FIGS. 1 to 6, the metaphysis and diaphysis areas are generally straight. This can be seen in particular on the inside lateral face of the prosthesis as shown in FIG. 4: the median line 5 of the inside lateral face is substantially contained within the transverse plane, and therefore appears straight in the figure.

In the preferred embodiment, shown in FIGS. 7 and 8, the proximal segment H2 of the proximal area of the rod 1 is substantially straight in the anterior-posterior plane, whereas the distal segment H1 of the proximal area is curved with the centre of curvature offset towards the front. The curvature can be seen more clearly in the lefthand part of FIG. 8. The distal area H3 of the rod 1 is substantially straight in this same anterior-posterior plane. It has been found that this embodiment improves the stability and the centring of the prosthesis in the femur. The drawings of FIGS. 7 and 8 are fairly accurate representations of the relative proportions of a typical prosthesis of the invention, and its dimension on a scale of about 0.7.

The neck 2 has an anteversion, shown by the section A in FIG. 1. The anteversion is defined by the angle K between the transverse plane and the axis of the neck 2. The anteversion angle K of the neck 2 is advantageously about 10°.

By virtue of the shape of a prosthesis of this kind, in most cases it is not necessary to use cement to seal the prosthesis rod into the medullary canal.

This avoids the problems associated with the presence of the cement: increased fitting time and operative morbidity, production of an exothermic reaction which among other things causes necrosis of the bone in contact with the cement during fitting, growth of fibrous tissues between the cement and the bone, and abnormal wear of the prosthesis due to movement of cement debris, which reduces its durability.

The shape of the proximal or metaphysis area with the double spiral twist procures strong anterior-posterior immobilisation of the prosthesis.

Wave-shape patterns in relief can be provided in the proximal or metaphysis part to enhance the stability of the prosthesis. These patterns increase the surface area of bone-implant contact, without preventing possible extraction by the surgeon. These patterns also create contact surface portions perpendicular to the axis of the bone, to take axial loads. These patterns can take the form of undulating peripheral ribs.

The present invention is not limited to the embodiments specifically described, but includes variants and generalisations thereof within the scope of the following claims.

We claim:

1. Hip prosthesis including a rod adapted to be inserted and fixed into the medullary canal of a femur, a neck joined to the upper end of the rod to join it to a spherical joint head, the rod having an oblong transverse section proximal area extending from the upper end on either side of an external shoulder to a transition area below the external shoulder and followed by a distal area, the rod being curved in the lateral plane with a centre of curvature offset towards the sagittal plane, the proximal area of the rod having a curved portion, in the anterior-posterior plane, with the centre of curvature offset towards the front, wherein the oblong transverse section proximal area comprises two adjacent segments with opposite spiral twists:

- a proximal segment having a righthanded spiral twist in a prosthesis for a right femur, and a lefthanded spiral twist in a prosthesis for a left femur,
- a distal segment having a lefthanded spiral twist in a prosthesis for a right femur, and a righthanded spiral twist in a prosthesis for a left femur.

2. Hip prosthesis according to claim 1, wherein the proximal segment and the distal segment of the oblong transverse section proximal area are joined together substantially in the area containing the external shoulder.

3. Hip prosthesis according to claim 1, wherein the proximal segment has a spiral twist with an angle between about 9° and about 13°.

4. Hip prosthesis according to claim 3, wherein the proximal segment has a spiral twist with an angle equal to about 11°.

5. Hip prosthesis according to claim 1, wherein the distal segment has a spiral twist with an angle between about 3° and about 6°.

6. Hip prosthesis according to claim 5, wherein the distal segment has a spiral twist with an angle equal to about 5°.

7. Hip prosthesis according to claim 1, wherein the distal segment is slightly shorter than the proximal segment.

8. Hip prosthesis according to claim 1, wherein the proximal segment of the proximal area of the rod is substantially straight, in the anterior-posterior plane, whereas the distal segment of the proximal area of the rod is curved with the centre of curvature offset towards the front.

9. Hip prosthesis according to claim 1, wherein the distal area of the rod is substantially straight in the anterior-posterior plane.

10. Hip prosthesis according to claim 1, wherein the neck (2) has an anteversion of about 10°.

* * * * *

UNITED STATES PATENT AND TRADEMARK OFFICE
CERTIFICATE OF CORRECTION

PATENT NO. : 6,030,417
DATED : February 29, 2000
INVENTOR(S) : Bresler et al.

It is certified that error appears in the above-identified patent and that said Letters Patent is hereby corrected as shown below:

Col. 2, line 54, change "FIG. 1 shows" to --FIGS. 1 and 1A-1L show--
Col. 3, line 1, change "FIG. 7 is" to --FIGS. 7 and 7A-7L are--
Col. 3, line 5, change "FIG. 8 is" to --FIGS. 8 and 8A-8L are--
Col. 3, line 25, change "A" to --1A, 7A, 8A--
Col. 3, line 26, change "B" to --1B, 7B, 8B--
Col. 3, line 26, change "C" to --1C, 7C, 8C--
Col. 3, line 27, change "D" to --1D, 7D, 8D--
Col. 3, line 27, change "E" to --1E, 7E, 8E--
Col. 3, line 28, change "F" to --1F, 7F, 8F--
Col. 3, lines 48 and 49, change "A, B, C and D" to --1A, 1B, 1C and 1D--
Col. 3, line 51, change "A, B, C and D" to --7A, 7B, 7C and 7D--
Col. 3, line 56, change "D, E and F" to --1D, 1E and 1F--
Col. 3, line 58, change "D, E and F" to --7D, 7E and 7F--
Col. 4, line 38, change "A" to --1A--

UNITED STATES PATENT AND TRADEMARK OFFICE
CERTIFICATE OF CORRECTION

PATENT NO. : 6,030,417
DATED : February 29, 2000
INVENTOR(S) : Bresler et al.

It is certified that error appears in the above-identified patent and that said Letters Patent is hereby corrected as shown below:

Claim 1, col. 5, line 4, change "to the upper end" to --to an upper end--
Claim 1, col. 5, lines 8 and 9, change "lateral plane" to --frontal plane--
Claim 1, col. 5, line 11, change "anterior-posterior plane" to --sagittal plane--
Claim 1, col 5, line 16, change "and a lefthanded spiral" to --or a lefthanded spiral--
Claim 1, col. 5, line 19, change "and a righthanded spiral" to --or a righthanded spiral--
Claim 2, col. 5, line 24, change "the area" to --an area--
Claim 8, col. 6, line 15, change "anterior-posterior plane" to --sagittal plane--
Claim 9, col. 6, lines 19 and 20, change "anterior-posterior plane" to --sagittal plane--

Signed and Sealed this

Twenty-seventh Day of February, 2001

Attest:

NICHOLAS P. GODICI

*Attesting Officer*   *Acting Director of the United States Patent and Trademark Office*